(12) United States Patent
Verkaart et al.

(10) Patent No.: US 7,754,494 B1
(45) Date of Patent: Jul. 13, 2010

(54) APPARATUS FOR THE STERILE TRANSFER OF FLUIDS

(75) Inventors: Wesley H Verkaart, Duxbury, MA (US); John R. Wells, La Jolla, CA (US); Lin A. Jakary, legal representative, La Jolla, CA (US); Lou Blasetti, North Quincy, MA (US); Steven M. Gann, Huntington Beach, CA (US)

(73) Assignee: Harvest Technologies Corporation, Plymouth, MA (US)

( * ) Notice: Subject to any disclaimer, the term of this patent is extended or adjusted under 35 U.S.C. 154(b) by 1313 days.

(21) Appl. No.: 09/623,793

(22) PCT Filed: Mar. 11, 1999

(86) PCT No.: PCT/US99/05287

§ 371 (c)(1),
(2), (4) Date: Sep. 8, 2000

(87) PCT Pub. No.: WO99/45851

PCT Pub. Date: Sep. 16, 1999

Related U.S. Application Data

(60) Provisional application No. 60/077,568, filed on Mar. 11, 1998.

(51) Int. Cl.
*G01N 33/00* (2006.01)

(52) U.S. Cl. .................. 436/180; 422/99; 422/100; 422/104

(58) Field of Classification Search .............. 422/100, 422/102, 99, 104; 436/180; 604/191, 199, 604/232, 89
See application file for complete search history.

(56) References Cited

U.S. PATENT DOCUMENTS

| 1,649,022 | A | 11/1927 | Eisele |
| 2,847,996 | A | 8/1958 | Cohen et al. |
| 2,860,635 | A | 11/1958 | Wilburn |
| 3,008,570 | A | 11/1961 | Roehr et al. |
| 4,212,309 | A | 7/1980 | Moorehead |
| 4,338,980 | A | 7/1982 | Schwebel et al. |
| 4,508,123 | A | 4/1985 | Wyatt et al. |
| 4,583,978 | A | 4/1986 | Porat et al. |
| 4,890,626 | A | 1/1990 | Wang |
| 5,332,092 | A | 7/1994 | Fischer |
| 5,769,825 | A * | 6/1998 | Lynn ................... 604/191 |
| 5,997,811 | A * | 12/1999 | Esposito ................... 422/1 |

* cited by examiner

*Primary Examiner*—Sam P Siefke
(74) *Attorney, Agent, or Firm*—Clark & Brody (57) ABSTRACT

A method, and apparatus for transferring a fluid to a sterile field includes the use of a sterile enclosure (58, 68) housing a syringe (40). The enclosure (58, 68) is made in two parts, and allows the syringe (40) to be operated while it is in the enclosure. When it is desired to pass the fluids to the sterile field, the enclosure is separated into at least two parts to allow the syringe to be removed. This removal of the syringe is done such that the user in the non-sterile field does not touch the syringe. Thus, the syringe, and fluid therein are easily transferred to the sterile field.

12 Claims, 8 Drawing Sheets

APPARATUS FOR THE STERILE TRANSFER OF FLUIDS

TECHNICAL FIELD

"This application is the national stage of International Application Number PCT/US1999/005287, filed Mar. 11, 1999, which was published in English, and claims priority of U.S. Provisional Application Number 60/077,568, filed Mar. 11, 1998."

This invention relates to the art of devices used for collecting fluids in a sterile manner while in a non-sterile field, maintaining the sterility of the fluids, and then transferring the fluids so collected to a sterile field. In particular, the invention relates to a syringe for use in collecting and transferring physiological fluids from a non-sterile field to a sterile field.

BACKGROUND

A surgical suite is physically divided between a "sterile field" and a "non-sterile field." The sterile field comprises the patient, the doctors and attending nurses, the equipment required for the procedure, and the physical portion of the suite occupied by this personnel and equipment. While the non-sterile field can be defined broadly as the area not in the sterile field, it is generally considered to comprise the personnel and equipment in an area adjacent the sterile field where tasks directly associated with the surgery are conducted. A problem often confronted during surgery is the maintenance of sterile conditions in the sterile field when passing items from the non-sterile field to the sterile field.

In one technique for passing an article from the non-sterile field to the sterile field, the article is sterilized and brought to the non-sterile field in a container that maintains the sterility. The container is opened by a person in the non-sterile field without touching the article. The container is then held adjacent the boundary (which may be imaginary) so that the article may be removed from the container by one in the sterile field. This technique is generally satisfactory. A particular problem, however, has been the transfer of sterile fluids to the sterile field.

A known technique for the transfer of fluids to the sterile field includes withdrawing the fluids into a syringe in a known, sterile manner, carrying the syringe of fluid to the boundary of the sterile field, and discharging the fluid from the syringe into a container in the sterile field. Discharge of the fluids into an open container, however, carries the risk that some of the fluids will be spilled and, thus, lost. In some instances, the needle of the syringe is inserted into the port of a container in the sterile field, but this is problematic because these ports are small and hard to engage. Further, the container is often held by a person in the sterile field, and this presents the risk that the needle will inadvertently be brought into contact with the person holding the container. This risks transmission of diseases to the person in the sterile field.

SUMMARY OF THE INVENTION

The method and apparatus of the invention provide collection of fluids in a non-sterile field and efficient, safe transfer of those fluids to the sterile field. While the invention finds particular use in connection with the production of autologous fibrinogen as described in U.S. Pat. No. 5,707,331, it may be used for the transfer of virtually any fluid in a sterile manner. For example, the system of the invention may be used to transfer to a sterile field such fluids as thrombin, cryoprecipitate, and fibrinogen. These materials may, further, be autologous or not.

In accordance with the procedures relating to fibrinogen as described in the noted patent, blood obtained from a patient is treated to remove the fibrinogen, which is then combined with thrombin and applied to the patient as a sealant. Because the equipment for treating the blood is located in the non-sterile field, transfer of the fibrinogen to the sterile field presents a problem to which this invention is addressed.

An apparatus in accordance with the invention comprises a syringe held in an outer casing in such a manner that the syringe can be used for collection of fluids, for example autologous fibrinogen, and then passed to personnel in the sterile field while retaining the casing in non-sterile field. In addition, the casing provides means whereby the plunger in the syringe can be operated repeatedly without compromising sterility.

In the preferred embodiment, the apparatus of the invention includes a syringe removably mounted in a cylindrical outer casing. The casing comprises two main parts, which may be separated to allow a syringe to be inserted and removed. The first part is generally cylindrical and receives the barrel part of the syringe. A second part is detachable from the first part and engages one end of the plunger of the syringe. When the two parts are secured to each other with the syringe therein, the syringe is maintained in a sterile condition. The second part of the casing is flexible whereby the plunger of the syringe may be operated while maintaining the sterility of the syringe. In one embodiment, the second part includes a bellows for allowing the plunger of the syringe to be moved linearly within the syringe barrel while maintaining the sterility of the syringe. In a second embodiment, the second part comprises a highly flexible envelope in the form of a "bag." The length of this envelope is such that it extends from the connection with the first part to the plunger the when the plunger is in an extended position, as when the syringe is filled. The bag is flexible enough to easily fold over on itself when the plunger is depressed, as in the initial, empty condition.

In a preferred embodiment, the method of the invention includes the steps of drawing material into a sterile syringe held in a casing while in the non-sterile field, opening the casing to expose the syringe and holding the casing such that the syringe can be grasped by a person in the sterile field and removed from the casing, or dropped into the sterile field. Then, the syringe in the sterile field is operated to dispense the material in the sterile field. The material is preferably fibrinogen that has been separated from a patient's blood.

DETAILED DESCRIPTION OF THE PREFERRED EMBODIMENTS

Figure 1:
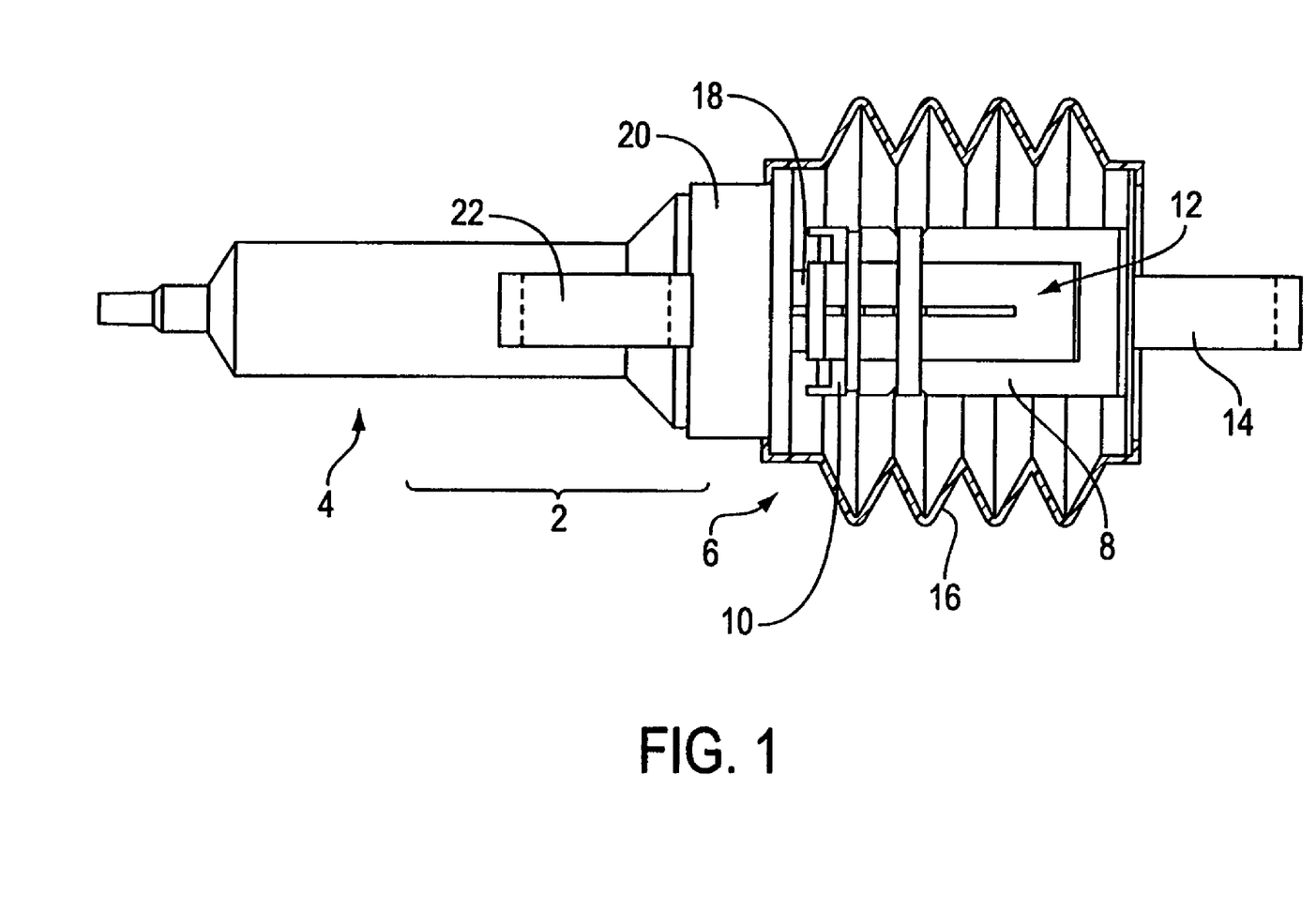
FIG. 1 is a top view in partial cross section of a first embodiment of an apparatus in accordance with the invention.
Figure 2:
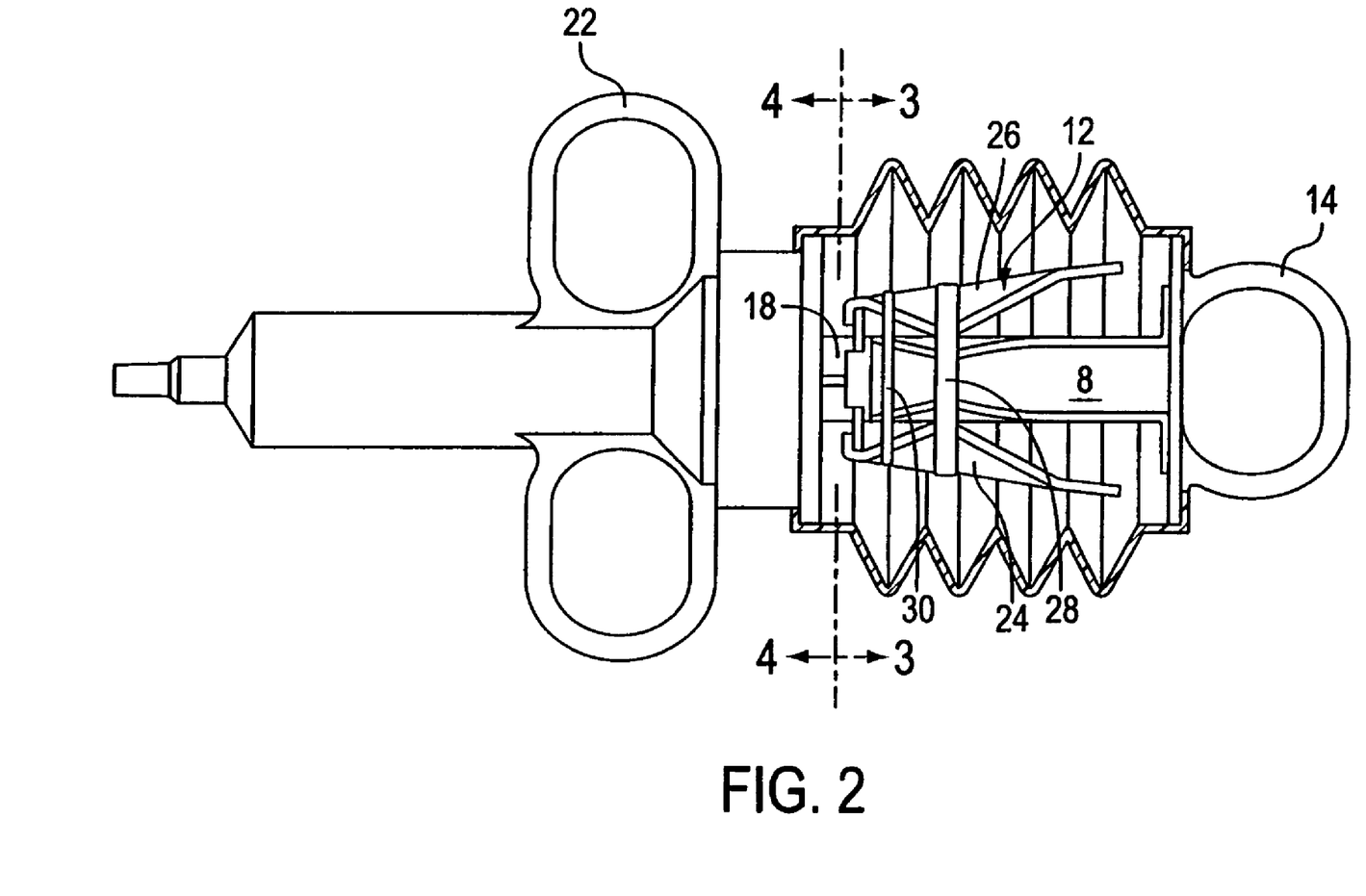
FIG. 2 is a side view of the apparatus of FIG. 1 in partial cross section.

With reference to FIG. 1, a first embodiment of an apparatus in accordance with the invention includes an outer casing 2 for receiving and operating a syringe while maintaining the sterility of the syringe. The casing comprises a first part 4, which receives the barrel portion of the syringe, and a second part 6, which engages the plunger portion of the syringe. The first and second parts are connected to each other to form a receptacle for receiving the syringe, and they may be detached to allow removal of the syringe, as will be described more fully below.

The second part 6 of the casing includes a clamp 12 for releasable attachment to the end of the syringe plunger. This clamp is mounted on a shaft 8 adjacent a base 10 and a thumb knob 14, which receives a user's thumb. One end of a bellows 16 is attached to the outer end of the shaft 8, and the other end of the shaft, having the base 10, is attached to an end 18 of the syringe plunger. The other end of the bellows 16 is attached to a connector 20, which is removable from the first part. The bellows allows the plunger 18 to be moved linearly to draw fluid in or expel fluid from the syringe without loss of sterility of the syringe or the fluid. That is, the bellows is sterilized prior to use and provides a sterile, closed environment in which the plunger moves.

As illustrated, the bellows may be attached to the shaft 8 and the connector 20 by lapping the material of the bellows over a lip on the connector and a disk at the end of the shaft. Cement may be used to secure the bellows to these elements. Other methods of attachment will be apparent.

The first part includes finger grips 22, which are positioned on the first part to cooperate with the thumb knob 14 to allow a user to grasp the outer casing easily to control movement of the syringe plunger.

In the embodiment shown in FIGS. 1 through 6, the clamp 12 comprises gripping elements 24 and 26 pivotally connected to the shaft 8. For example, central parts of the gripping elements adjacent fulcrum portions may be held to the shaft by a band 28, and the respective tips are urged toward each other by an elastic band 30.

Figure 3:
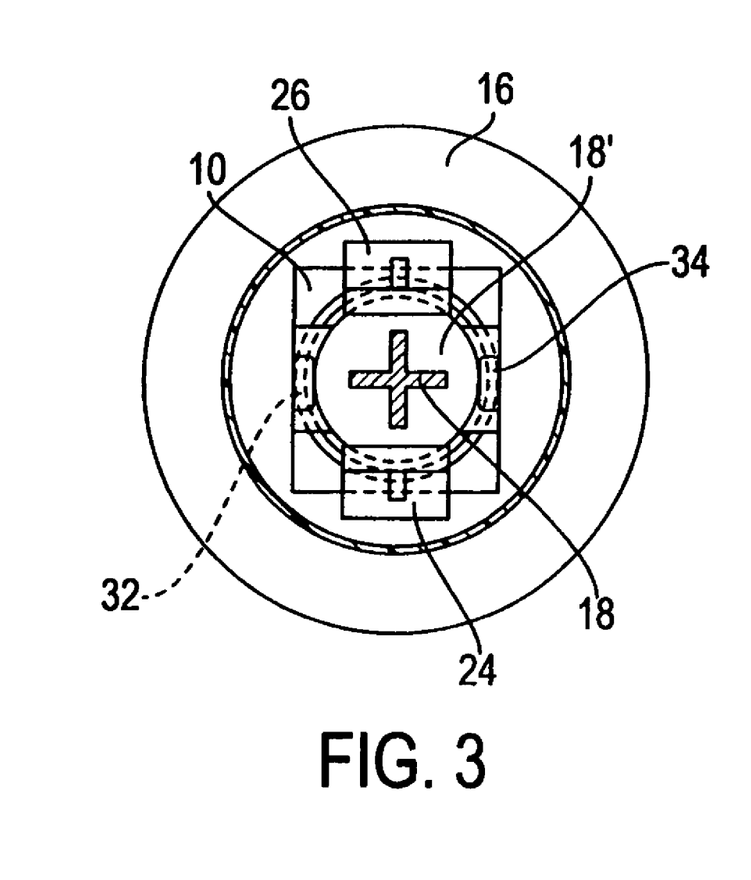
FIG. 3 is a cross section taken along line 3-3 of FIG. 2.

FIG. 3 shows the connection between the clamp 12 and the syringe plunger 18. The base 10 has stops 32 and 34 for engaging diametrically opposed parts of the end of the plunger 18, while the clamp elements 24 and 26 grip the end of the plunger at diametrically opposed locations rotationally displaced from those engaged by the stops 32 and 34. It will be appreciated that the stops prevent movement of the end of the plunger in the plane of the base 10 in one direction while the gripping elements 24 and 26 prevent movement in the plane of the base in a transverse direction and also secure the plunger to the base. Thus, the plunger will move linearly with movement of the shaft 8.

Figure 4:
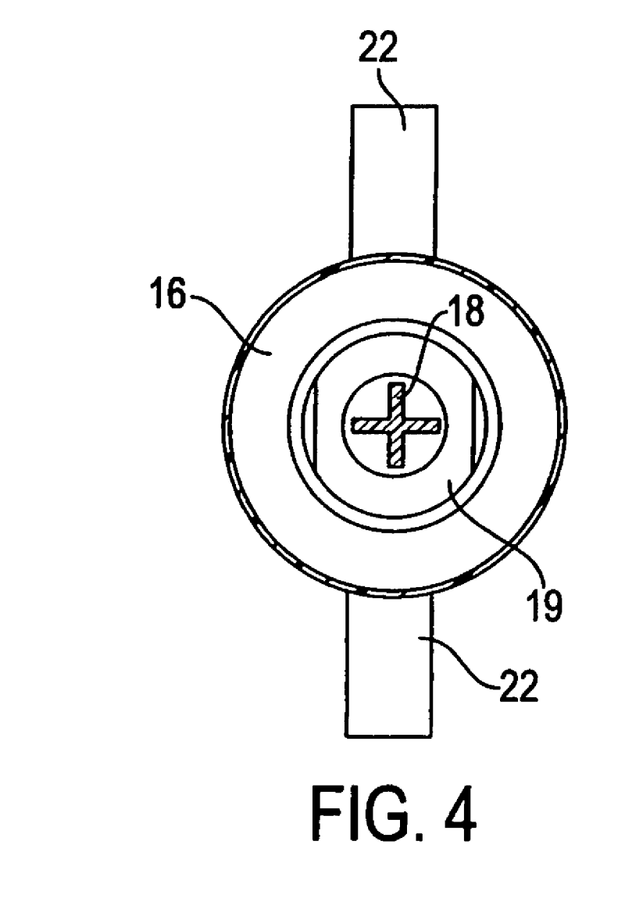
FIG. 4 is a cross section taken along line 4-4 of FIG. 2.

FIG. 4 illustrates how the flange of the syringe is received in a recess in the first part to secure the syringe rotationally.

Figure 5:
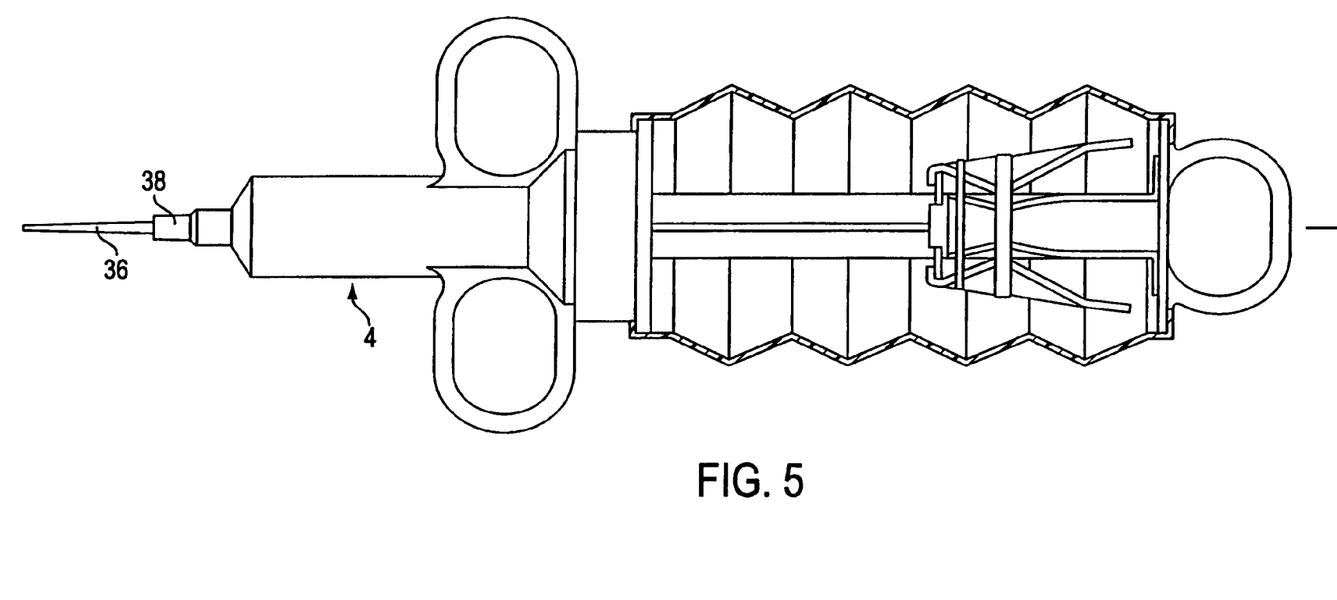
FIG. 5 is a side view of the apparatus of FIG. 1 in partial cross section and in an extended position.
Figure 6:
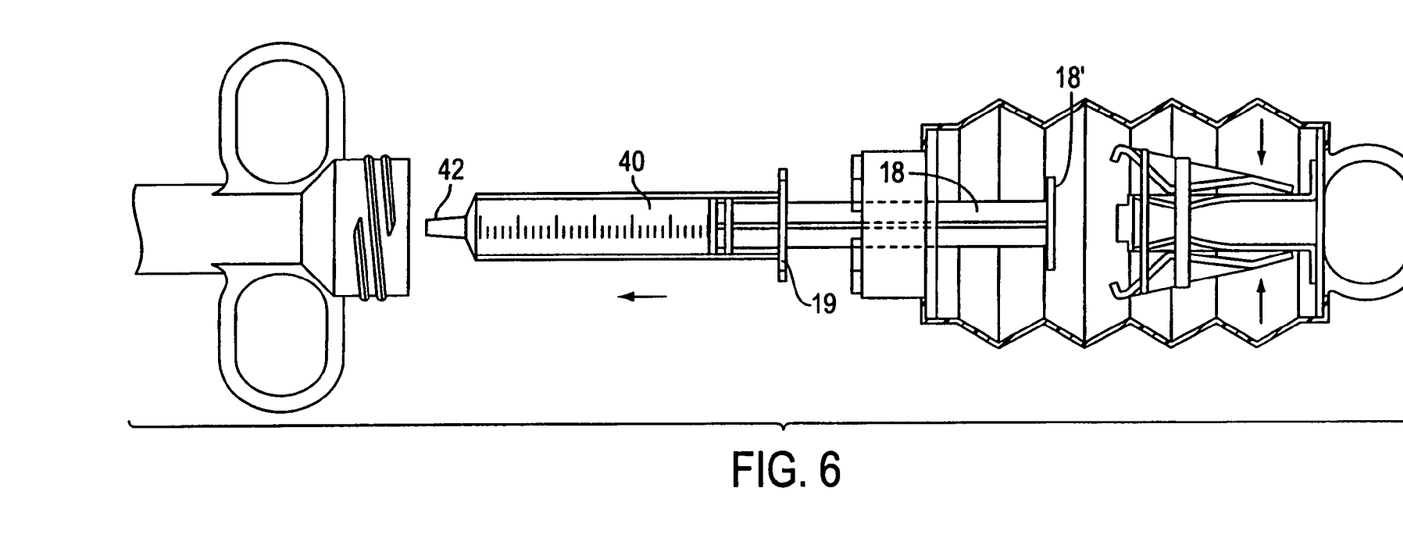
FIG. 6 is an exploded side view of the apparatus of FIG. 1.
Figure 7:
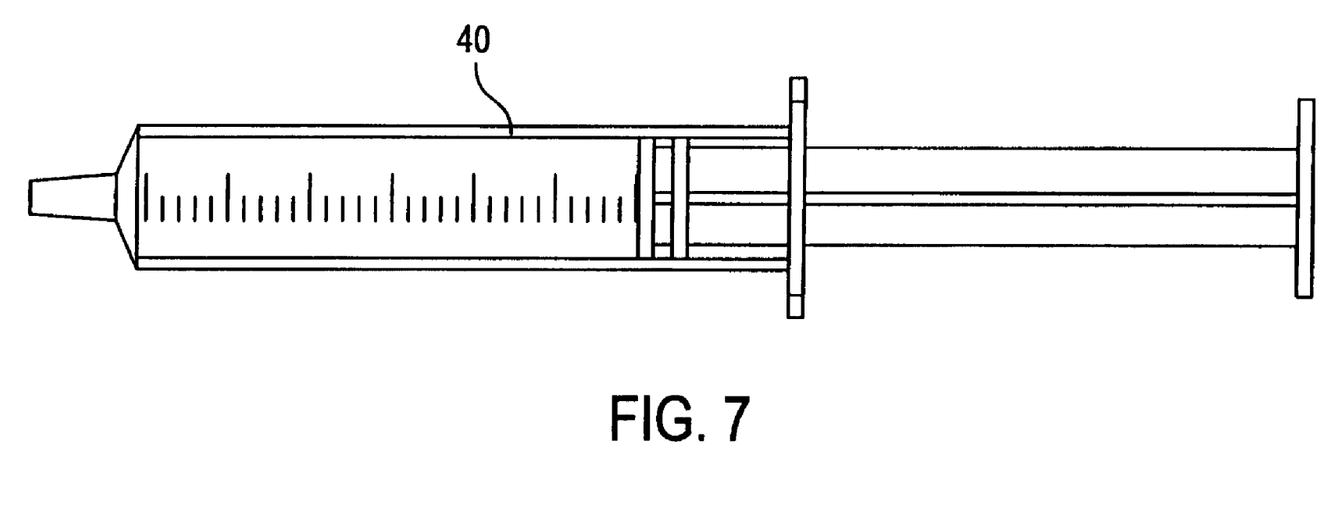
FIG. 7 is a side view of a syringe portion of the invention of FIG. 1.

FIGS. 5 through 7 illustrate how the described apparatus can be used in accordance with a method of the invention. A needle 36 is attached to the tip 38 of the first part 4. A syringe includes a barrel 40 and a plunger 18. The barrel is received in a cylindrical section of the first part 4 and includes a tip 42 that engages the tip 38 of the first part to provide a detachable but fluid-tight seal. Fluid is drawn in to the syringe by inserting the needle into the fluid and withdrawing the plunger, as illustrated in FIG. 5. A user can do this by inserting fingers in the finger grips 22, a thumb in the thumb knob 14, and pulling the thumb knob outwardly. Because the syringe is contained within the space created by the bellows, the plunger can be moved repeatedly to withdraw and expel the fluid to produce a mixing action.

Then, the casing is opened by detaching the connector 20 from the remainder of the first part while retaining the connection between the syringe and the shaft 8. This will allow the user to remove the syringe from the first part of the casing while touching only the connector, bellows, or thumb knob. Thus, the sterility of the syringe has been maintained. Then, the user can place the syringe into the sterile field by holding the thumb knob. A person in the sterile field can than grasp the syringe while the user releases the clamp elements 12 as shown in FIG. 6. This release is accomplished by squeezing the clamping elements together through the flexible bellows. The syringe of fluid is then available for use in the sterile field as shown in FIG. 7.

Figures 8, 9:
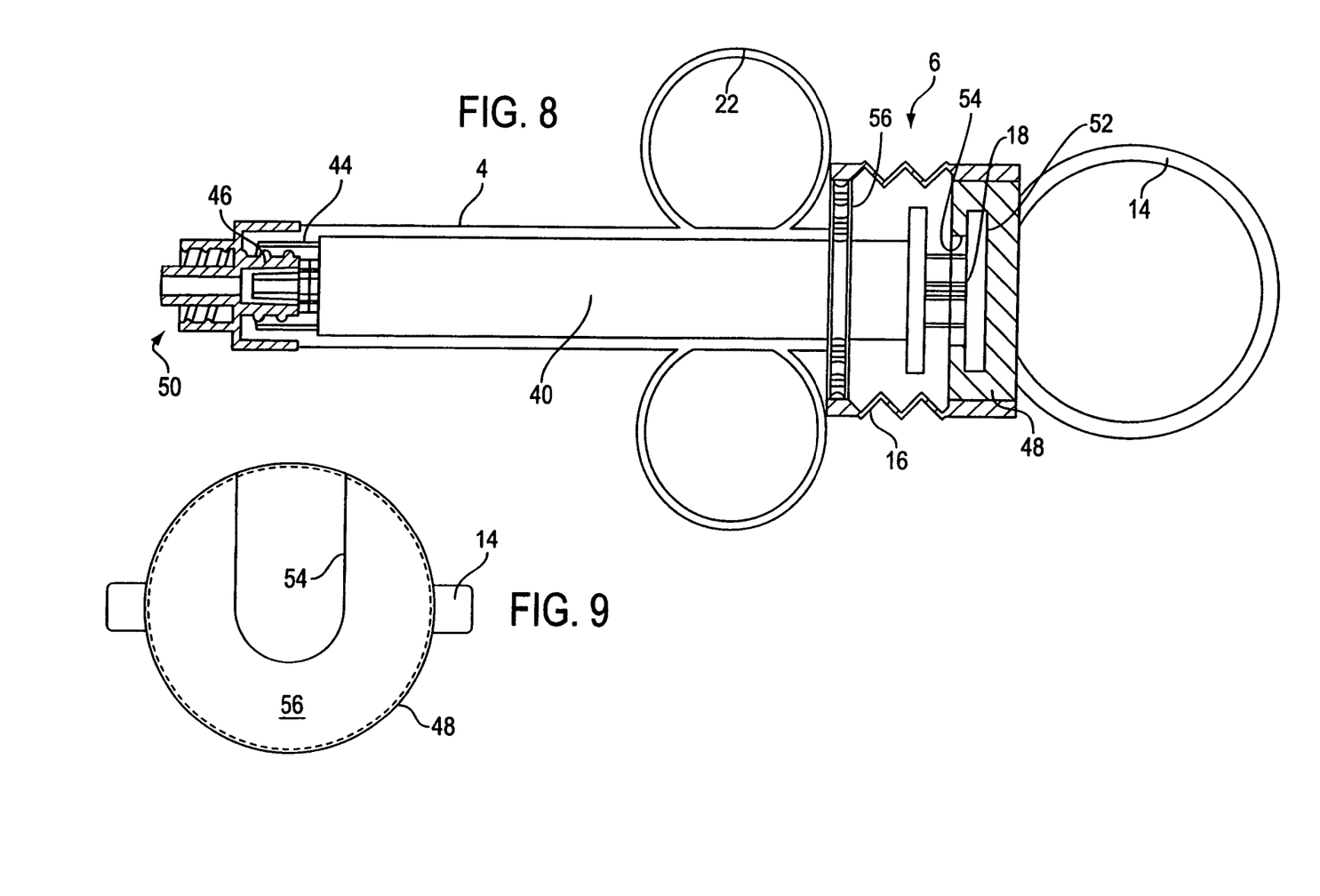
FIG. 8 is a transverse cross section of a second embodiment of an apparatus in accordance with the invention.
FIG. 9 is a bottom view of the connector element of the embodiment of FIG. 8.

In the embodiment of FIGS. 1 through 7, the connection between the tip 42 of the syringe and the tip 38 of the first part of the casing is a lap joint. That is, the interior surface of the tip 38 is conical and the exterior surface of tip 42 is conical. These conical surfaces fit closely together to form a seal. FIG. 8 illustrates a second embodiment wherein the syringe 40 includes a threaded, male Luer lock connector 44. The outer casing includes a threaded female connector 46 that cooperates with male connector 44 to securely connect the two elements. These threaded elements are preferably in the form of the Luer connector commonly used in medical equipment.

A male Luer lock connector 50 is provided on the exterior of the first part 4 of the outer casing for removably receiving a needle such as that shown at 36 in FIG. 5. Such a needle would be provided with a female Luer lock as known in the art.

The embodiment of FIG. 8 also provides an alternate connection between the thumb knob 14 and the end of the syringe plunger 18. In this embodiment, the plunger 18 is received in a connector 48 such that the plunger may be reciprocated during withdrawal of a fluid into the syringe 40 and detached during transfer of the syringe. With reference to FIG. 9, it will be appreciated that connector 48 includes a recess 50 for receiving the head 18' of the plunger 18. The plunger shaft is received in a slot 54 in a lower surface 56 of the connector 48.

The slot 54 opens to the side of the connector 48 to allow the head 18' of the plunger to be detached from the connector by sliding the plunger outwardly. The bellows 16 is attached to a side surface of the connector above the slot 54 and is flexible enough to allow the head to be removed from the recess 50 by sliding the plunger along the slot 54.

The end of the bellows 16 that is attached to the first part 4 of the outer casing is resilient and is received in an annular groove in a flange portion 56 of the part 4. The bellows may be detached from the flange by pulling it out of the groove. Preferably, this end of the bellows is provided with a tab for facilitating engagement by the fingers of a user. Alternatively, the end of the bellows is held in the groove by a band that must be removed before detaching the bellows.

Thus, the embodiment shown in FIGS. 8 and 9 is operated much like the first embodiment. That is, the fluid to be transferred is withdrawn into the syringe 40 by moving the thumb knob outward. Then, the bellows is released from the flange 56 and the connector is detached from the plunger. These steps are accomplished with the user holding the outer casing in one hand and the thumb knob or bellows in the other and without touching the syringe. After exposing the syringe; the user extends it into the sterile filed, whereupon one in the sterile field releases it from the Luer lock and removes the syringe. Alternatively, the user releases the syringe from the Luer lock by engaging the syringe through the bellows and twisting it. The bellows is then removed, and the syringe allowed to slide from the casing and onto a receiving surface in the sterile field.

Figure 10:
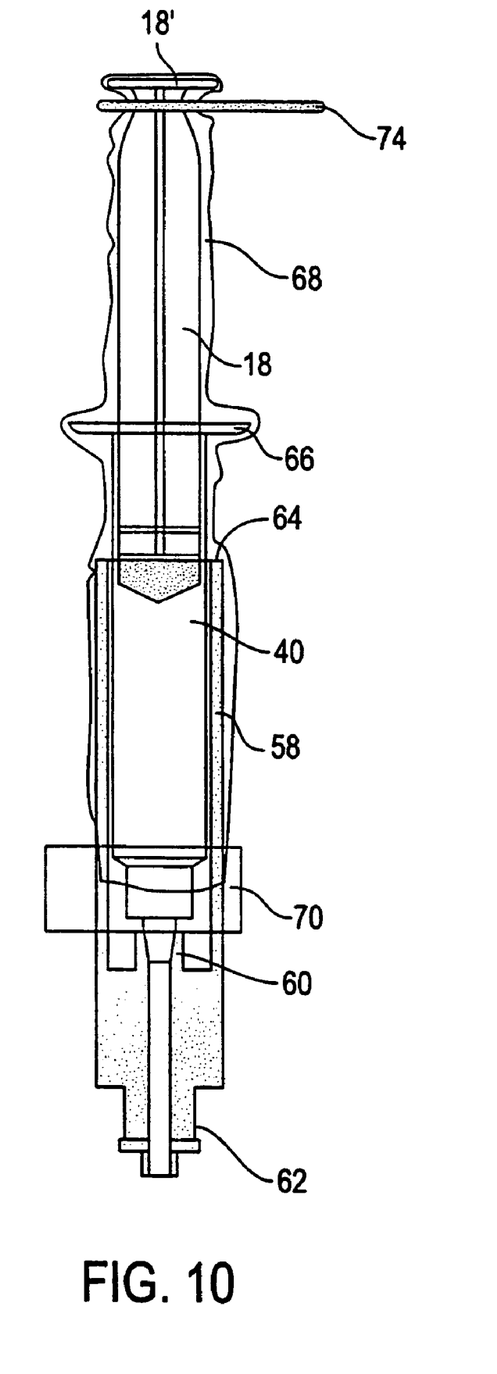
FIG. 10 is a vertical cross section of a third embodiment of the invention with the plunger extended.
Figure 11:
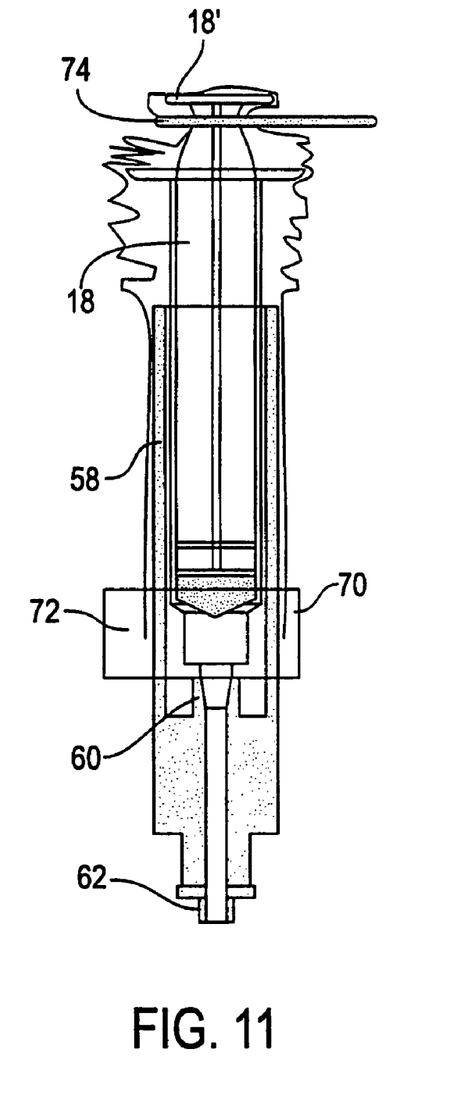
FIG. 11 is a vertical cross section of the third embodiment with the plunger depressed.

The embodiment of FIGS. 10 and 11 is preferred because of its ease of manufacture. According to this embodiment, the first part of the outer casing is a rigid or semi-rigid tube 58 with a closed end fitted with internal and external Luer connectors 60 and 62, respectively. Preferably, the length of the tube 58 is such that its upper end 64 lies slightly below the finger flanges 66 of the syringe barrel 40.

The tube 58 is preferably made of transparent or highly translucent plastic, such as polycarbonate, polyester, polyethylene, polypropylene, styrene, acrylic, or similar materials.

The second part of the outer casing in this embodiment comprises a thin, flexible envelope 68. This envelope is in the form of a highly flexible bag sealed on three sides and open at one end. The open end fits over the finger tabs 66 and over the outside diameter of the rigid tube 58. The length of the bag is such that it completely encloses the plunger, finger flanges, and upper part of the rigid tube 58. The bag is preferably made of transparent plastic, such as polyethylene film, with a thickness of 1 to 4 mils.

The open end of the bag 68 is secured to the tube 58 with an air-tight seal strip 70. The seal strip includes a pull tab 72 that facilitates grasping by the user for removal of the seal strip and release of the envelope 68 from the tube 58.

The seal strip may be adhesive-backed tape, perforated tape, an elastic strip, or a shrink-wrapped strip. The pull tab 72 may be colored to contrast with the remainder of the strip for easy location by the user.

A retainer 74 may be placed at the upper end of the envelope to hold it to the plunger to facilitate the user's grasping the plunger. The retainer may be a flexible plastic clip in the form of a horseshoe, an elastic o-ring, or the like, that is easily removed from the bag and plunger during transfer of the syringe to the sterile field. The retainer may be of any of a variety of materials, such as nylon, rubber, and the like.

FIG. 11 illustrates the syringe with the plunger in the empty position. The envelope is fully collapsed in this condition. In the condition shown in FIG. 11, there is a given amount of air in the envelope. As the plunger is withdrawn, the air contained in the syringe barrel is expelled into the envelope so that there is no necessity for air to enter or leave the envelope during motion of the plunger. This absence of venting assists in ensuring maintenance of sterility.

The operation of the embodiment shown in FIGS. 10 and 11 is the same as that illustrated in FIGS. 5 through 7. That is, a needle 36 is attached to the connector 62, and the plunger 18 is withdrawn to draw fluid into the syringe. Then, the seal strip 70 is removed, and the syringe removed from the tube 58 by twisting to disengage the Luer or other lock 60, with the user holding the syringe by the plunger through the envelope 68. Then, the tube is handed to a second user in the sterile field and the envelop is released from the plunger by detaching the retainer 74. Another technique would be to release the retainer and seal strip, grasp the plunger through the envelope in one hand and the tube 58 in the other, twist the two to release the lock 60, and then remove the envelope. The syringe can then be presented to a second user in the sterile field for removal from the tube 58. Or the envelope can be removed and the syringe presented to the second user, who twists the syringe to release the lock and remove it from the tube.

It will be appreciated that selected features of each of the embodiments shown may be employed in the other embodiment. Thus, the Luer connectors of the embodiment of FIGS. 8 and 9 may be used in the embodiment of FIGS. 1 through 7.

The articles described herein are preferably made of plastic and may be manufactured with any of a variety of techniques, including, for example, injection molding, blow molding, extrusion and other known techniques.

Modifications within the scope of the appended claims will be apparent to those of skill in the art.

We claim:

1. Apparatus for transferring a fluid to a sterile field comprising a casing having a first part and a second part, wherein said casing is configured to receive a syringe containing said fluid and maintain sterility of said syringe when said first part is connected to said second part, said syringe may be removed from said casing when said first part is disconnected from said second part, said first part is adapted to receive a barrel portion of said syringe and allow sterile, fluid communication with said syringe from a non-sterile field outside said casing, said second part is adapted to receive a plunger portion of said syringe, and said second part is flexible in the direction of movement of said plunger and configured to allow a user to engage and manipulate said plunger when said syringe is in said casing and said first and second parts are connected, wherein said first part includes a connector that detachably engages a tip of said syringe and allows said fluid communication between said syringe and the exterior of said casing, and said first part is readily detachable from said second part wherein the first part is a rigid tube and includes gripping elements.

2. Apparatus according to claim 1 wherein said second part is a bellows.

3. Apparatus according to claim 1 wherein said second part is made of a thin flexible sheet.

4. Apparatus according to claim 3 wherein said thin flexible sheet is in the shape of a bag.

5. Apparatus according to claim 1 wherein said first part is adapted to receive only part of said barrel portion and said second part is adapted to receive said plunger portion and a part of said barrel portion.

6. Apparatus according to claim 1 wherein said second part comprises means for releasable engagement of said plunger and a thumb knob that can be engaged by a user's thumb.

7. Apparatus according to claim 6 wherein said means for releasable engagement comprises a clamp.

8. Apparatus according to claim 6 wherein said means for releasable engagement comprises a disc with a slot for receiving an end of said plunger.

9. Apparatus according to claim 1 wherein said connector provides a lap joint between said casing and said syringe inlet.

10. Apparatus according to claim 1 wherein said connector provides a Luer connector between said casing and said syringe inlet.

11. Apparatus according to claim 1 wherein said connector provides a Luer connector on the exterior of said casing for engaging a needle located in the non-sterile field.

12. Apparatus according to claim 3 wherein said flexible sheet allows a user to grasp said syringe through said flexible sheet.

* * * * *